(12) United States Patent
Bitsch-Larsen

(10) Patent No.: US 10,843,995 B2
(45) Date of Patent: Nov. 24, 2020

(54) PROCESSES FOR MANUFACTURING AROMATIC CARBOXYLIC ACIDS

(71) Applicant: BP Corporation North America Inc., Houston, TX (US)

(72) Inventor: Anders Bitsch-Larsen, Wheaton, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 16/627,214

(22) PCT Filed: Jun. 19, 2018

(86) PCT No.: PCT/US2018/038206
§ 371 (c)(1),
(2) Date: Dec. 27, 2019

(87) PCT Pub. No.: WO2019/005532
PCT Pub. Date: Jan. 3, 2019

(65) Prior Publication Data
US 2020/0123092 A1    Apr. 23, 2020

Related U.S. Application Data

(60) Provisional application No. 62/526,885, filed on Jun. 29, 2017.

(51) Int. Cl.
*C07C 51/265* (2006.01)
*C07C 51/43* (2006.01)

(52) U.S. Cl.
CPC .......... *C07C 51/265* (2013.01); *C07C 51/43* (2013.01)

(58) Field of Classification Search
CPC .................. C07C 51/265; C07C 51/43
See application file for complete search history.

(56) References Cited

U.S. PATENT DOCUMENTS

| | | | |
|---|---|---|---|
| 2,741,369 A | 4/1956 | Fest | |
| 3,859,344 A * | 1/1975 | Shigeyasu | B01J 19/1862 562/414 |
| 4,835,307 A | 5/1989 | Lindahl et al. | |
| 5,723,656 A | 3/1998 | Abrams | |
| 6,137,001 A | 10/2000 | Broeker et al. | |
| 7,807,060 B2 | 10/2010 | Schmid | |
| 7,935,844 B2 | 5/2011 | Bartos | |
| 7,935,845 B2 | 5/2011 | Bartos et al. | |
| 8,173,834 B2 | 5/2012 | Bartos | |
| 2005/0051473 A1 | 3/2005 | Suss et al. | |
| 2012/0220800 A1* | 8/2012 | Bartos | B01D 3/009 562/414 |
| 2014/0171679 A1 | 6/2014 | Shih et al. | |
| 2015/0182890 A1 | 7/2015 | Keyes et al. | |
| 2015/0183705 A1* | 7/2015 | Metelski | C07C 51/42 562/413 |

FOREIGN PATENT DOCUMENTS

| | | | |
|---|---|---|---|
| GB | 1 350 874 A | 4/1974 | |
| GB | 1 555 246 A | 11/1979 | |
| WO | 02/098836 A1 | 12/2002 | |
| WO | WO-02098836 A1 * | 12/2002 | ............ C07C 63/26 |
| WO | 2016014830 A1 | 1/2016 | |

* cited by examiner

*Primary Examiner* — Paul A Zucker
(74) *Attorney, Agent, or Firm* — McDonnell Boehnen Hulbert & Berghoff LLP

(57) ABSTRACT

A process for manufacturing a carboxylic acid is provided, in one aspect, the process comprises oxidizing a feedstock comprising a substituted aromatic hydrocarbon to form a liquid-phase aromatic carboxylic acid; crystallizing at least a portion of the liquid-phase aromatic carboxylic acid in the presence of oxygen and an oxidation catalyst in a first crystallizer to form solid aromatic carboxylic acid, under reaction conditions suitable to oxidize unreacted feedstock to form additional aromatic carboxylic acid; and crystallizing at least a portion of the first crystallization effluent in the presence of oxygen and an oxidation catalyst in a second crystallizer to form additional solid aromatic carboxylic acid, under reaction conditions suitable to oxidize unreacted feedstock to form additional aromatic carboxylic acid, wherein the oxygen is present in a gaseous phase inside the second crystallizer in an amount of no more than 11% by volume on a dry basis.

15 Claims, 2 Drawing Sheets

PROCESSES FOR MANUFACTURING AROMATIC CARBOXYLIC ACIDS

CROSS-REFERENCE TO RELATED APPLICATIONS

This application is a U.S. National Phase Application under 35 U.S.C. § 371 of International Application No. PCT/US2018/038206, filed Jun. 19, 2018, which claims priority to U.S. Provisional Application No. 62/526,885, filed Jun. 29, 2017, the contents of which are incorporated herein by reference in their entirety.

TECHNICAL FIELD

The present disclosure relates generally to processes for manufacturing aromatic carboxylic acids.

BACKGROUND

Terephthalic acid and other aromatic carboxylic acids are widely used in manufacture of polyesters, commonly by reaction with ethylene glycol, higher alkylene glycols or combinations thereof, for conversion to fiber, film, containers, bottles and other packaging materials, and molded articles.

In commercial practice, aromatic carboxylic acids are commonly made by liquid phase oxidation in an aqueous monocarboxylic acid solvent of methyl-substituted benzene and naphthalene feedstocks, in which the positions of the methyl substituents correspond to the positions of carboxyl groups in the desired aromatic carboxylic acid product, with air or another source of oxygen, which is normally gaseous, in the presence of a bromine-promoted catalyst comprising cobalt and manganese. The oxidation is exothermic and yields aromatic carboxylic acid together with by-products, including partial or intermediate oxidation products of the aromatic feedstock, and acetic acid reaction products, such as methanol, methyl acetate, and methyl bromide. Water is also generated as a by-product.

Aromatic carboxylic acids, typically accompanied by oxidation by-products of the feedstock, are commonly formed dissolved or as suspended solids in the liquid phase reaction mixture and are commonly recovered by crystallization and solid-liquid separation techniques. The exothermic oxidation reaction is commonly conducted in a suitable reaction vessel at elevated temperature and pressure, with the oxygen concentration in the reactor being monitored and controlled. A liquid phase reaction mixture is maintained in the vessel and a vapor phase formed as a result of the exothermic oxidation is evaporated from the liquid phase and removed from the reactor to control reaction temperature. The vapor phase comprises water vapor, vaporized monocarboxylic acid solvent and small amounts of by-products of the oxidation, including both solvent and feedstock by-products. It usually also contains oxygen gas not consumed in oxidation, minor amounts of unreacted feedstock, carbon oxides and, when the oxygen source for the process is air or another oxygen-containing gaseous mixture, nitrogen, carbon oxides and other inert gaseous components of the source gas.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids with reduced levels of impurities can be made by further oxidizing crude products from liquid phase oxidation as described above, to convert feedstock partial oxidation products to the desired acid product.

In conventional processes, crude products from a liquid phase oxidation, performed in a suitable reaction vessel, are crystallized in a first crystallizer of a series of crystallizers. Notably, the crystallization is performed in the first crystallizer in the presence of oxygen, which can oxidize any unreacted or partially-oxidized feedstock. Oxygen is conventionally fed to such a first crystallizer in a concentration similar to that in the reaction vessel, typically greater than 20% by volume on a dry basis in a feed stream. The product of the first crystallizer may, in conventional processes, be further crystallized in one or more additional crystallizers in the substantial absence of additional oxygen. In such processes, however, the reaction conditions of the reaction vessel necessarily remain harsh in order to maintain a high reaction yield, which can cause an undesirable extent of impurity formation.

Accordingly, there remains a need for a process for a more efficient process of manufacturing aromatic carboxylic hydrocarbons with reduced levels of impurities.

SUMMARY

The scope of the present disclosure is defined solely by the appended claims, and is not affected to any degree by the statements within this summary.

According to one aspect of the disclosure, a process for manufacturing a carboxylic acid is provided. The process includes oxidizing a feedstock comprising a substituted aromatic hydrocarbon in a reaction zone in the presence of an oxidation catalyst and a solvent under reaction conditions suitable to form a reaction mixture comprising a liquid-phase aromatic carboxylic acid, the reaction zone providing a reaction zone effluent comprising the liquid-phase aromatic carboxylic acid;

crystallizing at least a portion of the liquid-phase aromatic carboxylic acid of the reaction zone effluent in the presence of oxygen and an oxidation catalyst in a first crystallizer of a crystallization zone to form solid aromatic carboxylic acid, under reaction conditions suitable to oxidize unreacted and/or partially oxidized feedstock in the reaction zone effluent to form additional aromatic carboxylic acid, the first crystallizer providing a first crystallization effluent; and crystallizing at least a portion of the first crystallization effluent in the presence of oxygen and an oxidation catalyst in a second crystallizer of the crystallization zone to form additional solid aromatic carboxylic acid, under reaction conditions suitable to oxidize unreacted and/or partially oxidized feedstock in the first crystallizer effluent to form additional aromatic carboxylic acid, the second crystallizer providing a second crystallization effluent, wherein the oxygen is present in a gaseous phase inside the second crystallizer in an amount of no more than 11% by volume on a dry basis.

Other aspects of the disclosure will be apparent to those skilled in the art in view of the description that follows.

DETAILED DESCRIPTION

Figure 1:
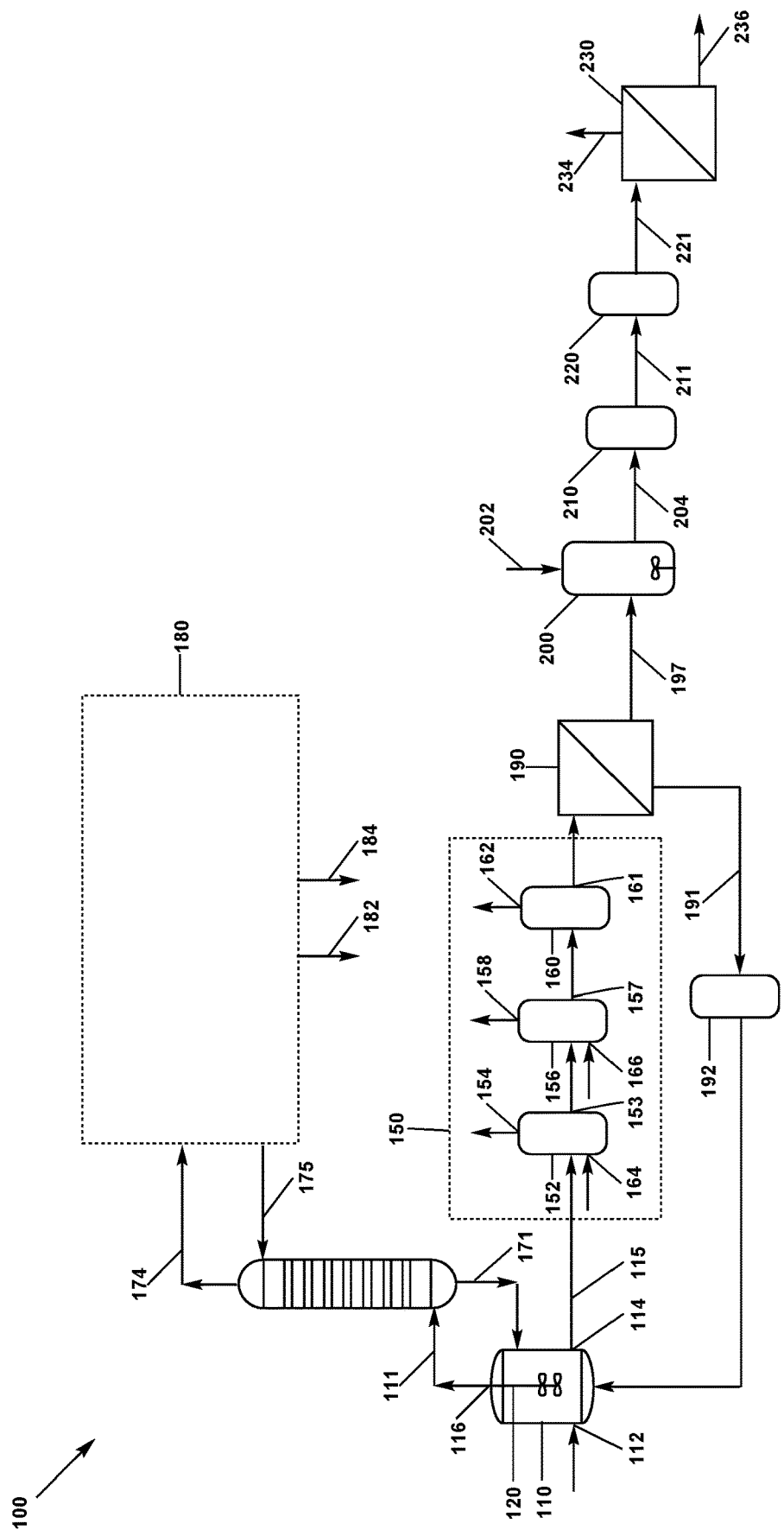
FIG. 1 is a process flow diagram for the manufacture and recovery of purified forms of aromatic carboxylic acids in accordance with one embodiment of the present disclosure.

In various aspects, the processes of the disclosure provide an efficient manner of manufacturing aromatic carboxylic hydrocarbons with reduced levels of impurities.

Additional features of the processes of the disclosure will now be described in reference to the drawing figures.

FIG. 1 is a process flow diagram for manufacturing and recovering aromatic carboxylic acids in accordance with one embodiment of the present disclosure.

In one aspect of the disclosure, a process includes oxidizing a feedstock (provided at inlet 112) comprising an alkyl aromatic hydrocarbon in a reaction zone (here, in oxidation reactor 110) in the presence of an oxidation catalyst and a solvent under reaction conditions suitable to form a reaction mixture including a liquid-phase aromatic carboxylic acid. The reaction zone provides (e.g., at outlet 114) a reaction zone effluent comprising the liquid-phase aromatic carboxylic acid. At least a portion of the liquid-phase aromatic carboxylic acid of the reaction zone effluent is crystallized in the presence of oxygen and an oxidation catalyst in a first crystallizer 152 of a crystallization zone 150 to form solid aromatic carboxylic acid, under reaction conditions suitable to oxidize unreacted and/or partially reacted feedstock in the reaction zone effluent to form additional aromatic carboxylic acid. The first crystallizer provides a first crystallization effluent (e.g., at 153). At least a portion of the first crystallization effluent is crystallized in the presence of oxygen and an oxidation catalyst in a second crystallizer 156 of the crystallization zone 150 to form additional solid aromatic carboxylic acid, under reaction conditions suitable to oxidize unreacted feedstock in the first crystallizer effluent to form additional aromatic carboxylic acid. The second crystallizer provides a second crystallization effluent (e.g., at 157). The oxygen is present in a gaseous phase inside the second crystallizer in an amount of no more than 11% by volume on a dry basis.

FIG. 1 depicts a number of additional elements for use in processes according to certain embodiments of the disclosure. A system for performing a process 100 of FIG. 1 includes a reaction zone that includes an oxidation reactor 110 configured for liquid-phase oxidation of feedstock to provide a reaction zone effluent; a crystallization zone 150 configured for forming solid crude aromatic carboxylic acid from the reaction zone effluent, and comprising first, second, and third crystallizers (152, 156, and 160, respectively) in series; a solid-liquid separation device 190 configured for separating solid crude aromatic carboxylic acid (and oxidation by-products) from liquid; a mixing zone including a purification reaction mixture make-up vessel 200 configured for preparing mixtures of crude aromatic carboxylic acid in purification reaction solvent; a purification zone including a hydrogenation reactor 210 configured for contacting the crude aromatic carboxylic acid with hydrogen in the presence of a catalyst to form a purified aromatic carboxylic acid; a recovery zone comprising a crystallization zone 220 including at least one crystallizer configured for forming a slurry stream comprising solid purified aromatic carboxylic acid and a vapor stream, wherein the vapor stream comprises steam and hydrogen; and a solid-liquid separation device 230 configured for separating solid purified aromatic carboxylic acid from liquid.

However, the person of ordinary skill in the art will appreciate that the integration of processes in FIG. 1 is meant to be purely representative, and various other integrated and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams of compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

As described above, the feedstock includes a substituted aromatic hydrocarbon. Representative feedstock materials suitable for use in the processes of the disclosure include but are not limited to aromatic hydrocarbons substituted at one or more positions with at least one substituent that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene; methylacetophenone; 1,2,4-trimethylbenzene; 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present disclosure are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) of aromatic rings that, in some embodiments, are fused (e.g., naphthalene, anthracene, etc.) and, in other embodiments, are not. In some embodiments, the aromatic carboxylic acid comprises only one carboxylic acid (e.g., —$CO_2H$) moiety or a salt thereof (e.g., —$CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be performed in the oxidation zone (e.g., oxidation reactor 110) is a liquid phase oxidation that comprises contacting oxygen gas and a feed material comprising an aromatic hydrocarbon having one or more substituents oxidizable to carboxylic acid groups in a liquid phase reaction mixture. In some embodiments, the liquid phase reaction mixture comprises a monocarboxylic acid solvent (e.g., acetic acid) and water in the presence of an oxidation catalyst comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in the reaction zone, e.g., in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air, as a source of oxygen, may be continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reaction zone, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized monocarboxylic acid, water vapor, gaseous by-products from the oxidation reaction, carbon oxides, nitrogen from the air charged to the reaction, unreacted oxygen, and the like, and combinations thereof.

The gaseous stream may be removed from the reactor through vent 116 and sent in a stream 111 to a distillation column 170. The distillation column 170 is configured to separate water from the solvent monocarboxylic acid and return a monocarboxylic acid-rich liquid phase to the reactor in stream 171. A water-rich gaseous stream is removed from the distillation column 170 in stream 174 and sent for further processing to an off-gas treatment zone 180. Reflux is returned to the distillation column 170 in stream 175. The reflux liquid may include a condensed, liquid phase component 182 of the water-rich gaseous stream 174, or may include fluid from other sources, such as liquid stream 234.

The person of ordinary skill in the art will appreciate that the off-gas treatment zone can include a variety of components, for example, one or more of a condenser, a disengagement drum configured to separate the effluent of the condenser into a gas-phase component and a liquid-phase component; a scrubber configured to remove impurities (e.g., alkyl aromatic hydrocarbons, solvent monocarboxylic acid) from the gas-phase component; a catalytic oxidation ("catox") unit configured to remove impurities (e.g., organic components, HBr) from the gas-phase component; a bromine scrubber, configured to remove bromine from the gas-phase effluent of the catox unit; and an expander and a turbine, configured to convert energy from the gas-phase component to electricity. The components of the off-gas treatment zone may be arranged in a number of configurations. For example, the gas-phase effluent of the high-pressure bromine scrubber may be sent to the expander and turbine. In another example, the gas-phase effluent of the absorber may be sent to the expander and turbine. In yet another example, the gas-phase effluent of the disengagement drum may be sent to the expander and turbine. A liquid-phase component 182 is removed from the off-gas treatment zone 180, and may include the liquid-phase effluent of the disengagement drum or the scrubber. A gas-phase component 184 is removed from the off-gas treatment zone 180, and may include the gas-phase effluent of the disengagement drum, the absorber, the high-pressure bromine scrubber, or the expander and turbine.

Figure 2:
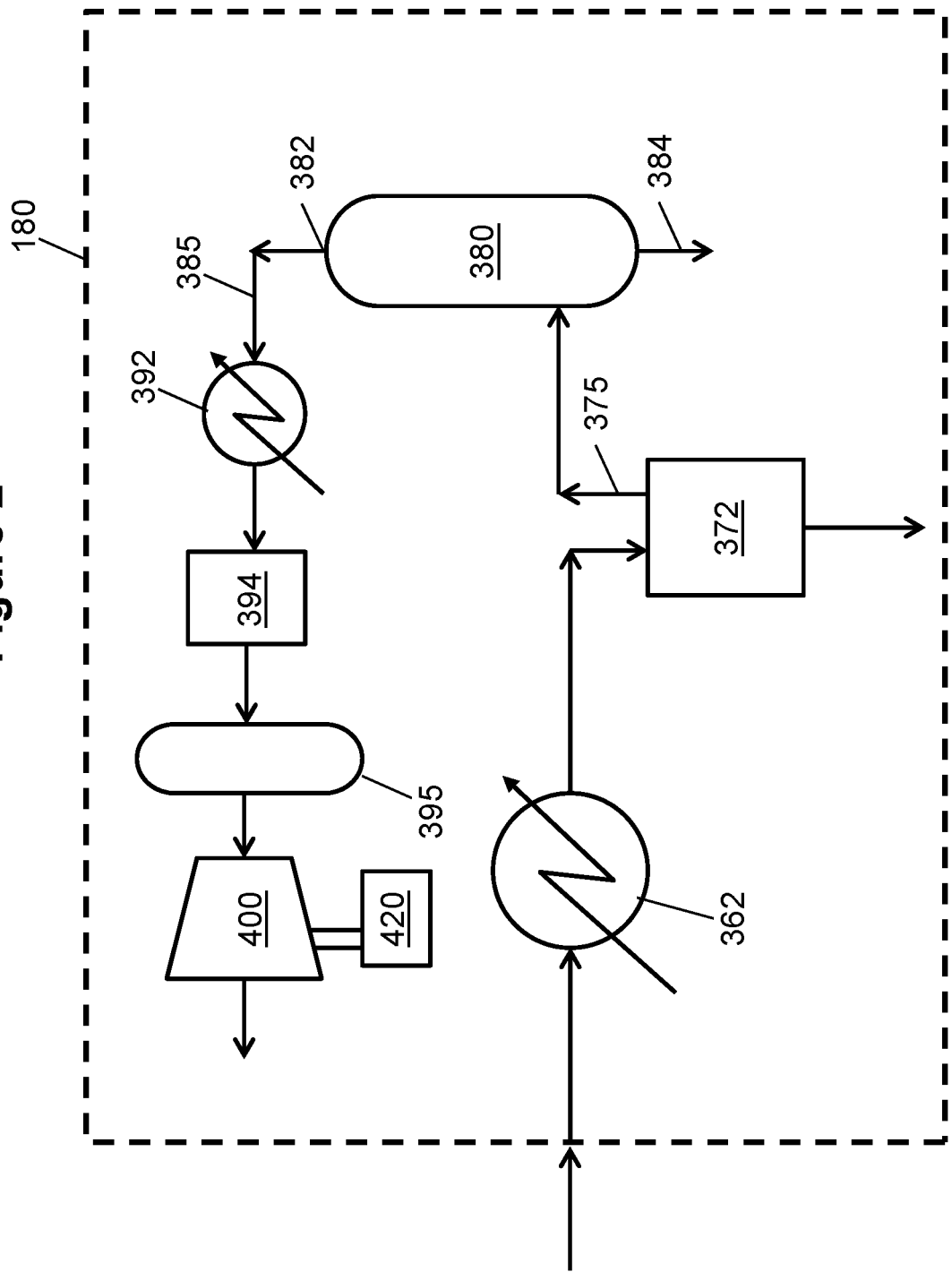
FIG. 2 is a process flow diagram for off-gas treatment in accordance with one embodiment of the present disclosure.

An example of a process flow for an off-gas treatment zone 180 is provided in FIG. 2. Off-gas treatment zone 180 includes a condenser 352, and disengagement drum 372. Gas and liquid effluent from condenser 362 is directed to drum 372, in which condensate liquid comprising water is collected and removed in stream 373, which can be directed to other uses or to a purge stream. A condenser exhaust gas under pressure is withdrawn as in stream 375. Condensation using two or more condensers in series using heat exchange fluids at successively lower temperatures allows for generation of steam at different pressures, thereby allowing for efficiencies in use of steam at the different pressures by matching with differing heat or energy inputs to operations in which steam is used.

Uncondensed exhaust gas from condensation removed in stream 375 comprises incondensable components such as unconsumed oxygen from oxidation, nitrogen from the air used as oxygen source to the oxidation, carbon oxides from such air as well as from reactions in oxidation, and traces of unreacted para-xylene and its oxidation by-products, as well as acetic acid, methyl acetate, and methanol, and methyl bromide formed from the bromine promoter used in oxidation. In certain embodiments, the uncondensed gas is substantially free of water vapor owing to substantially complete condensation into the condensate liquid recovered in the condenser.

The uncondensed exhaust gas from can be, for example, under pressure of about 10 to about 15 kg/cm$^2$ and can be transferred directly to a power recovery device or to a pollution control device for removing corrosive and combustible species in advance of power recovery. In the embodiment of FIG. 2, uncondensed gas is first directed to treatment to remove unreacted feed materials and traces of solvent acetic acid and/or reaction products thereof remaining in the gas. Thus, uncondensed gas is transferred in stream 375 to high pressure absorber 380 for absorbing para-xylene, acetic acid, methanol and methyl acetate without substantial loss of pressure. Absorber 380 is adapted for receipt of the substantially water-depleted gas remaining after condensation and for separation of para-xylene, solvent acetic acid and its reaction products from oxidation from the gas by contact with one or more liquid scrubbing agents. The absorber also includes an upper vent 382 from which a scrubbed gas under pressure comprising incondensable components of the inlet gas to the absorber is removed in stream 385 and a lower outlet 384 for removal of a liquid acetic acid stream into which components from the gas phase comprising one or more of para-xylene, acetic acid, methanol and/or methyl acetate have been scrubbed. A bottoms liquid can be removed from a lower portion of the absorber and directed to the reaction zone for reuse of recovered components.

Pressurized gas from the condenser 362, or, as depicted in FIG. 2, from the vent 382 from the high pressure absorber, can be treated for pollution control, for example, to convert organic components and carbon monoxide in the gas from the condenser or the absorber to carbon dioxides and water. Such treatment can be performed, for example, using a catalytic oxidation unit adapted for receiving the gas, optionally heating it to promote combustion and directing the gas into contact with a high temperature-stable catalyst disposed on a cellular or other support. Overhead gas from absorber 380 can be, for example, directed to oxidation unit 394, optionally being preheated by one or more preheaters 392.

An oxidized high pressure gas is directed from catalytic oxidation unit 394 to expander 400 which is connected to generator 420. Energy from the oxidized high pressure gas can be converted to work in the expander 400 and such work is converted to electrical energy by generator 420. Expanded gas exits the expander and can be released to the atmosphere, preferably after caustic scrubbing and/or other treatments for appropriately managing such releases. Before being directed to the expander 400, some or all of the high pressure gas can be directed to a bromine scrubber 395.

The person of ordinary skill in the art will appreciate that the off-gas treatment zone can be configured in a variety of manners. Examples of processing and treatment of the reaction off-gas stream, and sources of reflux fluids are more fully described in U.S. Pat. Nos. 5,723,656, 6,137,001, 7,935,844, 7,935,845, and 8,173,834.

In some embodiments, solid crude product may be recovered from the reaction zone effluent by crystallization in one or more stages, such as in a series of multiple stirred crystallizers, as shown in FIG. 1. In the embodiment shown in FIG. 1, liquid-phase reaction mixture is removed from reaction vessel 110 through slurry outlet 114 and directed in stream 115 to crystallizer 152 of a crystallization zone to provide solid oxidation product, and in turn, crystallizers 156 and 160 of the crystallization zone, to form additional solid oxidation product. In some embodiments, the crystallization process comprises sequential reductions in temperature and pressure from earlier to later stages to increase product recovery. For example, as shown in FIG. 1, crystallizers 152, 156, and 160 of a crystallization zone 150 may be provided in series and in fluid communication, such that product slurry from crystallizer 152 may be transferred to crystallizer 156, and that product slurry from crystallizer 156 may be transferred to crystallizer 160. Cooling in the crystallizers may be accomplished by pressure release. One or more of the crystallizers may be vented, as at vents 154, 158, and 162, to remove vapor resulting from pressure let down and generation of steam from the flashed vapor to a heat exchanger (not shown).

As described above, in various embodiments of the processes of the disclosure, the crystallization in the first crystallizer is performed in the presence of oxygen and an oxidation catalyst under reaction conditions suitable to oxidize unreacted feedstock in the reaction zone effluent to form additional aromatic carboxylic acid. For example, as in FIG. 1, air, as a source of oxygen, may be continuously charged to crystallizer 152 through an inlet, such as inlet 164. In certain embodiments as otherwise described herein, oxygen is fed to the first crystallizer in an oxygen-containing feed stream that comprises at least 15%, or even at least 20%, by volume on a dry basis. The oxidation catalyst can, for example, be oxidation catalyst from the reaction zone, directed to the first crystallizer along with the liquid aromatic carboxylic acid.

As described above, in various embodiments of the processes of the disclosure, the crystallization in the second crystallizer is performed in the presence of contains oxygen and an oxidation catalyst under reaction conditions suitable to oxidize unreacted feedstock in the first crystallizer effluent to form additional aromatic carboxylic acid. In various embodiments according to the present disclosure, oxygen is present in a gaseous phase inside the second crystallizer in an amount of no more than 11% by volume on a dry basis. For example, in certain embodiments of the processes as otherwise described herein, oxygen is present in a gaseous phase inside the second crystallizer in an amount of no more than 10%, or no more than 9%, or no more than 8%, or no more than 7%, or no more than 6%, or no more than 5% or no more than 4%, or no more than 2%, or no more than 1%, by volume on a dry basis. In certain such embodiments, oxygen is present in the gaseous phase in the second crystallizer in an amount of at least 0.3% by volume on a dry basis. The oxidation catalyst can, for example, be the oxidation catalyst from first crystallizer, directed to the first crystallizer along with the solid aromatic carboxylic acid.

In some embodiments, an oxygen-containing feed stream is fed to the second crystallizer (i.e., to provide oxygen to the crystallization). For example, in the embodiment shown in FIG. 1, an oxygen-containing feed stream may be continuously charged to second crystallizer 156 through one or more inlets, such as inlet 166. In some embodiments, an oxygen-containing feed stream comprising oxygen in an amount of no more than 11% by volume on a dry basis is fed to the second crystallizer. For example, in certain embodiments as otherwise described herein, an oxygen-containing feed stream comprising oxygen in an amount of no more than 10%, or no more than 9%, or no more than 8%, or no more than 7%, or no more than 6%, or no more than 5%, or no more than 4%, or no more than 3%, or no more than 2%, by volume on a dry basis is fed to the second crystallizer. In certain such embodiments, oxygen is present in the oxygen-containing feed stream in an amount of at least 0.3%, or at least 1% by volume on a dry basis.

Notably, the presently disclosed processes can improve product purity by allowing the initial oxidation reaction in the reactor zone to be performed under relatively gentler conditions as compared to conventional processes. While reaction conditions of the reaction zone of conventional processes for manufacturing an aromatic carboxylic acid are necessarily harsh to maintain a desirable reaction yield, the methods disclosed herein allow for the use of gentler reaction conditions in the reaction zone, which can reduce impurity formation in the reaction zone. Similarly, the methods disclosed herein can allow for the manufacture of a purer product under otherwise similar conditions as a result of the crystallization in the second crystallizer being performed as described herein.

In certain embodiments of the processes as otherwise described herein, the aromatic carboxylic acid prepared by the process comprises terephthalic acid, and the substituted aromatic hydrocarbon of the feedstock comprises para-xylene. For example, in certain such embodiments, the substituted aromatic hydrocarbon of the feedstock is at least 99% by weight para-xylene.

The oxygen can be provided to the crystallization in the second crystallizer in a number of manners. In certain embodiments of the processes as otherwise described herein, the process further includes treating at least a portion of a reaction off-gas recovered from the reaction zone in an off-gas treatment zone (e.g., as described above), and wherein at least a portion of the oxygen of the oxygen-containing feed stream comprises at least a portion of an oxygen-containing gas formed in the off-gas treatment zone. This can be provided, for example, as the gas-phase component 184 as identified in FIG. 1.

For example, in certain embodiments of the processes as otherwise described herein, the treating in the off-gas treatment zone includes separating the reaction off-gas to form a water-rich stream and a monocarboxylic acid solvent-rich stream; and separating at least a portion of the water-rich stream to form a gas-phase component comprising oxygen, and a liquid-phase component. At least a portion of the oxygen of the oxygen-containing feed stream (i.e., provided to the second crystallizer) includes at least a portion of the gas-phase component of the reaction off-gas. This can be performed, e.g., using the process described above with respect to FIG. 2. The oxygen-containing gas-phase component can be provided from any desirable point in the process, for example, downstream from an absorber, downstream from an oxidation unit, or downstream from a bromine scrubber.

In certain embodiments, the oxidation catalyst in the reaction zone includes bromine, and the process further comprises scrubbing the gas-phase component to remove bromine, the oxygen of the oxygen-containing feed stream comprising at least a portion of the gas-phase component remaining after said scrubbing. This can be performed, e.g., using the process described above with respect to FIG. 2. For example, in certain such embodiments, the oxygen of the gas-phase component comprises at least a portion of the gas-phase effluent of the high-pressure bromine scrubber 395 of off-gas treatment zone.

Of course, in other embodiments, the oxygen-containing feed stream provided to the crystallization in the second crystallizer is provided from a different part of the process. For example, in some embodiments, a flue gas is recovered from the first crystallizer and at least a portion of the oxygen of the oxygen-containing feed stream comprises at least a portion of the flue gas of the first crystallizer. For example, with respect to the process shown in FIG. 1, at least a portion of an oxygen-containing flue gas recovered from the first crystallizer 152 of the crystallization zone 150 can be provided to the crystallization in the second crystallizer. In certain such embodiments, at least a portion of an oxygen-containing flue gas is recovered from crystallizer 152 through one or more vents, such as vent 154. Effluent from vent 154 can be condensed and vapor routed to absorber 380.

In certain embodiments, part or all of the oxygen in the second crystallization is provided via a hydrogen peroxide-containing feed stream. As the person of ordinary skill in the art will appreciate, hydrogen peroxide can decompose to provide oxygen, especially under the conditions in the second crystallizer. Accordingly, in certain embodiments of the methods as otherwise described herein, a hydrogen peroxide-containing feed stream is fed to the second crystallizer.

The crystallization in the second crystallizer can be, in certain embodiments, performed at a lower pressure, a lower temperature, or a lower pressure and temperature than the crystallization in the first crystallizer. For example, in certain embodiments, the crystallization in the first crystallizer can be performed at a temperature in the range of 185-190° C., and a pressure of 10.5-11.5 barg, and the crystallization in the second crystallizer can be performed at a temperature in the range of 155-165° C., and a pressure of 3.5-4 barg.

Based on the present disclosure, the person of ordinary skill in the art can perform the processes of the disclosure to provide for low levels of impurities at the second crystallization effluent. For example, in certain embodiments of the processes as otherwise described herein, the second crystallization effluent includes 4-carboxybenzaldehyde in an amount of no more than 4500 ppm, e.g., no more than 3000 ppm, on a solids basis. Similarly, in certain embodiments of the processes as otherwise described herein, the second crystallization effluent includes p-toluic acid in an amount of no more than 750 ppm, e.g., no more than 500 ppm, on a solids basis.

The processes have thus far been described with respect to two crystallization operations, one performed in a first crystallizer and the other provided in the second crystallizer. Additional crystallizations can be used in the processes of the disclosure. For example, in certain embodiments as otherwise described herein, the process further includes crystallizing at least a portion of the second crystallization effluent in a third crystallizer of the crystallization zone to form a third crystallization effluent comprising solid aromatic carboxylic acid. For example, in the process illustrated in FIG. 1, the second crystallization effluent is crystallized in third crystallizer 160 to provide a third crystallization effluent (provided at 161). The process can optionally include additional crystallizations, performed in additional crystallizers in the crystallization zone. In certain desirable embodiments, when crystallizations subsequent to the first crystallization and the second crystallization are performed, they are performed without being fed a gaseous feed stream that includes at least 1% oxygen by volume on a dry basis. In certain desirable embodiments, when crystallizations beyond the first crystallization and the second crystallization are performed, they are performed at relatively low temperatures, e.g., less than 140° C. (e.g., 110-120° C.).

A variety of process operations can be used in recovery of the crystallized carboxylic acid. In certain embodiments as otherwise described herein, at least a portion of an effluent of a last crystallizer of the crystallization zone is separated to form an aromatic carboxylic acid-rich stream and a solvent-rich stream. For example, in the process depicted in FIG. 1, the crystallization zone 150 is in fluid communication with a solid-liquid separation device 190. The solid-liquid separation device 190 is configured to receive a slurry of solid product from the crystallization zone 150. In some embodiments, the solid-liquid separation device 190 is further configured to separate a crude solid product and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). Suitable rotary pressure filters are sold by BHS-Sonthofen and are disclosed for example, in U.S. Pat. Nos. 2,741,369, 7,807,060, U.S. Pat. App. 20050051473, US Pat. App. 20150182890, and WO 2016/014830. The oxidation mother liquor resulting from the separation may exit separation device 190 in solvent-rich stream 191 for transfer to mother liquor drum 192. A portion of the mother liquor and, in some embodiments, a major portion of the mother liquor, may be transferred from drum 192 to the reaction zone (e.g., to oxidation reactor 110). In such a way, monocarboxylic acid solvent, water, catalyst, and/or oxidation reaction by-products dissolved and/or present as fine solid particles in the mother liquor may be returned to the liquid phase oxidation reaction.

As shown in FIG. 1, the aromatic carboxylic acid-rich stream 197 from the separation device 190 comprising crude solid product may be directed to a mixing zone including a reaction mixture make up vessel 200. The crude solid product in stream 197 may be mixed and slurried in make-up vessel 200 with a make-up solvent entering vessel 200 through line 202 to form a purification reaction mixture comprising crude aromatic carboxylic acid. The purification reaction mixture prepared in vessel 200 is withdrawn through line 204. In some embodiments, the purification make-up solvent contains water. In some embodiments, the solvent line 202 connects to a holding vessel (not shown) for containing make-up solvent. In other embodiments, the solvent comprises fresh demineralized water fed from a deaerator. In other embodiments, the solvent is supplied from another part of the integrated process 100. For example, in one embodiment, the solvent comprises liquid-phase component 182 of off-gas treatment zone 180. In another embodiment, the solvent comprises the liquid-phase stream 234 exiting solid-liquid separator 230. Sources of purification make-up solvent are more fully described, for example, in U.S. Pat. Nos. 5,723,656, 6,137,001, 7,935,844, 7,935,845, and 8,173,834.

In certain embodiments as otherwise described herein, at least a portion of the aromatic carboxylic acid-rich stream is purified in a purification zone comprising a hydrogenation catalyst under reaction conditions suitable to form a purification effluent comprising purified aromatic carboxylic acid. For example, in the process depicted in FIG. 1, purification reaction mixture exiting vessel 200 through stream 204 enters purification reactor 210 of the purification zone. The purification zone may further include a pump and one or more heat exchangers (not shown) configured to pre-heat the purification mixture exiting vessel 200 before it enters purification reactor 210. In some embodiments, the purification reactor 210 is a hydrogenation reactor and purification in the purification reactor 210 comprises contacting the purification reaction mixture comprising crude aromatic carboxylic acid with hydrogen in the presence of a hydrogenation catalyst. In some embodiments, at least a portion of a purification effluent comprising purified aromatic carboxylic acid may be continuously removed from hydrogenation reactor 210 in stream 211 and directed to a crystallization zone 220 downstream of the purification zone. Crystallization zone 220 may comprise a plurality of crystallizers. In some embodiments, in crystallization zone 220, purified aromatic carboxylic acid and reduced levels of impurities may be crystallized from the reaction mixture. The resulting solid/liquid mixture comprising purified carboxylic acid solids formed in crystallization zone 220 may be fed, in stream 221, to a solid-liquid separation device 230, configured to separate the solid/liquid mixture into a liquid-phase stream 234 and an aromatic carboxylic acid-rich stream 236 comprising solid purified aromatic carboxylic acid.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for manufacturing an aromatic carboxylic acid, comprising:
    oxidizing a feedstock comprising a substituted aromatic hydrocarbon in a reaction zone in the presence of an oxidation catalyst and a solvent to form a reaction mixture comprising a liquid-phase aromatic carboxylic acid, the reaction zone providing a reaction zone effluent comprising the liquid-phase aromatic carboxylic acid;

crystallizing at least a portion of the liquid-phase aromatic carboxylic acid of the reaction zone effluent in the presence of oxygen and an oxidation catalyst in a first crystallizer of a crystallization zone to form solid aromatic carboxylic acid, and oxidizing unreacted and/or partially oxidized feedstock in the reaction zone effluent to form additional aromatic carboxylic acid, the first crystallizer providing a first crystallization effluent;

crystallizing at least a portion of the first crystallization effluent in the presence of oxygen and an oxidation catalyst in a second crystallizer of the crystallization zone to form additional solid aromatic carboxylic acid, and oxidizing unreacted and/or partially oxidized feedstock in the first crystallizer effluent to form additional aromatic carboxylic acid, the second crystallizer providing a second crystallization effluent, wherein a gaseous phase inside the second crystallizer comprises the oxygen in an amount of no more than 11% by volume of the gaseous phase on a dry basis; and feeding an oxygen-containing feed stream to the second crystallizer, the oxygen being present in the oxygen-containing feed stream in an amount of no more than 11% by volume of the feed stream on a dry basis.

2. The process of claim 1, wherein the oxygen is present in the oxygen-containing feed stream in an amount of no more than 5% by volume of the feed stream on a dry basis.

3. The process of claim 1, wherein the oxygen is present in the oxygen-containing feed stream in an amount of no more than 2% by volume of the feed stream on a dry basis.

4. The process of claim 1, further comprising
recovering a reaction off-gas from the reaction zone; and
treating at least a portion of the recovered reaction off-gas in an off-gas treatment zone; wherein at least a portion of the oxygen-containing feed stream is formed in the off-gas treatment zone.

5. The process of claim 4, wherein treating at least a portion of the recovered reaction off-gas comprises:
separating the reaction off-gas to form a water-rich stream and a monocarboxylic acid solvent-rich stream; and
separating at least a portion of the water-rich stream to form a gas-phase component comprising oxygen, and a liquid-phase component; and
wherein at least a portion of the oxygen of the oxygen-containing feed stream comprises at least a portion of the gas-phase component.

6. The process of claim 1, wherein the oxidation catalyst in the reaction zone comprises bromine, and wherein the process further comprises scrubbing the gas-phase component to remove bromine, the oxygen of the oxygen-containing feed stream comprising at least a portion of the gas-phase component remaining after said scrubbing.

7. The process of claim 1, wherein a flue gas is recovered from the first crystallizer through a vent, and at least a portion of the oxygen of the oxygen-containing feed stream comprises at least a portion of the flue gas of the first crystallizer.

8. The process of claim 1, further comprising feeding a hydrogen peroxide-containing feed stream to the second crystallizer.

9. The process of claim 1, further comprising crystallizing at least a portion of the second crystallization effluent in a third crystallizer of the crystallization zone to form a third crystallization effluent comprising solid aromatic carboxylic acid.

10. The process of claim 1, further comprising separating at least a portion of an effluent of a last crystallizer of the crystallization zone to form an aromatic carboxylic acid-rich stream and a solvent-rich stream.

11. The process of claim 10, further comprising purifying at least a portion of the aromatic carboxylic acid-rich stream in a purification zone comprising a hydrogenation catalyst to form a purification effluent comprising purified aromatic carboxylic acid.

12. The process of claim 1, wherein:
the aromatic carboxylic acid comprises terephthalic acid; and
the substituted aromatic hydrocarbon of the feedstock comprises para-xylene.

13. The process of claim 1, wherein the feedstock comprises at least 99% para-xylene.

14. The process of claim 13, wherein the second crystallization effluent comprises 4-carboxybenzaldehyde in an amount of no more than 4500 ppm on a solid basis, and comprises p-toluic acid in an amount of no more than 750 ppm on a solid basis.

15. The process of claim 1, wherein the gaseous phase inside the second crystallizer comprises the oxygen in an amount of at least 0.3% by volume of the gaseous phase on a dry basis.

* * * * *